(12) United States Patent
Zhu et al.

(10) Patent No.: US 10,123,533 B2
(45) Date of Patent: Nov. 13, 2018

(54) NITROGEN CONTAINING SURFACTANTS FOR AGRICULTURAL USE

(71) Applicant: AKZO NOBEL CHEMICALS INTERNATIONAL B.V., Amersfoort (NL)

(72) Inventors: Shawn Zhu, Stormville, NY (US); Joshua Jurs, New Fairfield, CT (US); Elliot Isaac Band, Pleasantville, NY (US); Michael Walters, Rhinebeck, NY (US)

(73) Assignee: AKZO NOBEL CHEMICALS INTERNATIONAL B.V., Arnhem (NL)

(*) Notice: Subject to any disclaimer, the term of this patent is extended or adjusted under 35 U.S.C. 154(b) by 0 days.

(21) Appl. No.: 14/822,116

(22) Filed: Aug. 10, 2015

(65) Prior Publication Data

US 2015/0342183 A1     Dec. 3, 2015

Related U.S. Application Data

(62) Division of application No. 13/392,615, filed as application No. PCT/EP2010/062601 on Aug. 30, 2010, now Pat. No. 9,137,988.

(60) Provisional application No. 61/239,086, filed on Sep. 2, 2009.

(30) Foreign Application Priority Data

Nov. 20, 2009   (EP) ..................... 09176575

(51) Int. Cl.
    *A01N 25/30*     (2006.01)
    *A01N 57/20*     (2006.01)

(52) U.S. Cl.
    CPC ............. *A01N 25/30* (2013.01); *A01N 57/20* (2013.01); *A01N 2300/00* (2013.01)

(58) Field of Classification Search
    None
    See application file for complete search history.

(56) References Cited

U.S. PATENT DOCUMENTS

| | | | |
|---|---|---|---|
| 3,307,931 A | 3/1967 | Unger et al. | |
| 5,118,444 A | 6/1992 | Nguyen | |
| 6,500,784 B1 * | 12/2002 | Mille | A01N 57/20 504/127 |
| 6,645,912 B1 | 11/2003 | Mille et al. | |
| 6,653,257 B2 | 11/2003 | Mille et al. | |
| 2003/0158042 A1 * | 8/2003 | Bramati | A01N 57/20 504/201 |
| 2004/0224846 A1 | 11/2004 | Bramati et al. | |
| 2005/0170965 A1 | 8/2005 | Bramati et al. | |
| 2008/0032083 A1 | 2/2008 | Serdy et al. | |
| 2008/0207456 A1 * | 8/2008 | Bergstrom | A01N 25/24 504/350 |

FOREIGN PATENT DOCUMENTS

| | | | |
|---|---|---|---|
| CA | 2 629 862 | 5/2007 | |
| CN | 1376029 A | 10/2002 | |
| CN | 1477928 A | 2/2004 | |
| CN | 1505479 A | 6/2004 | |
| CN | 1605253 A | 4/2005 | |
| EP | 1 541 023 A2 | 6/2005 | |
| EP | 2 025 230 A2 | 2/2009 | |
| EP | 2025230 A2 * | 2/2009 | ............. A01N 57/20 |
| EP | 2025230 A2 * | 2/2009 | ............. A01N 57/20 |
| GB | 1 398 276 | 6/1975 | |
| JP | H05-112403 A | 5/1993 | |
| JP | H10-505362 A | 5/1998 | |
| JP | 2002-530305 A | 9/2002 | |
| JP | 2004-051631 A | 2/2004 | |
| JP | 2006-076920 A | 3/2006 | |
| WO | 97/01281 A1 | 1/1997 | |
| WO | 00/30452 A1 | 6/2000 | |
| WO | WO-0030452 A1 * | 6/2000 | ............. A01N 57/20 |
| WO | WO 0030452 A1 * | 6/2000 | ............. A01N 57/20 |
| WO | WO 00/38523 | 7/2000 | |
| WO | WO 0038523 A1 * | 7/2000 | ............. A01N 57/20 |
| WO | 01/17346 A1 | 3/2001 | |
| WO | 02/26036 A1 | 4/2002 | |
| WO | 02/069718 A2 | 9/2002 | |
| WO | WO 03/063589 A2 | 8/2003 | |
| WO | WO 2006/069791 A1 | 7/2006 | |
| WO | WO 2006/111563 A1 | 10/2006 | |
| WO | WO 2006111563 A1 * | 10/2006 | ............. A01N 25/24 |
| WO | WO 2007/059107 A2 | 5/2007 | |
| WO | WO 2008/066611 A2 | 6/2008 | |
| WO | WO 2009/080225 A2 | 7/2009 | |
| WO | WO 2009/082675 A1 | 7/2009 | |

OTHER PUBLICATIONS

European Search Report for 09176575.0 dated Mar. 30, 2010.
International Search Report for PCT/EP2010/062601 dated Jun. 9, 2011.
Dean et al., "Surfactant effects on glyphosate efficacy," vol. 9, No. 2, pp. 281-285 (1995) XP 009131572.
Ethomeen T/12 MSDS dated May 25, 2006 [downloaded on May 12, 2014 from http://www.jacaab.com/msds/Ethomeen%20T12%20MSDS.pdf.

* cited by examiner

*Primary Examiner* — Thor Nielsen
(74) *Attorney, Agent, or Firm* — Matthew D. Kellam

(57) ABSTRACT

The present invention comprises formulations for agricultural use comprising a surfactant and pesticide. The surfactants comprise nitrogen containing surfactants with $N^+$—$CH_2COO^-$, $N^+$—$CH_2COOCH_3$, $N$—$CH_2COO^-M^+$, $N$—$CH_2CH_2COO^-M^+$, and/or amine oxide functionalities which enhance the pesticide activity. The pesticides include herbicides, fungicides and insecticides.

8 Claims, 7 Drawing Sheets

NITROGEN CONTAINING SURFACTANTS FOR AGRICULTURAL USE

CROSS-REFERENCE TO RELATED APPLICATIONS

This application is a divisional of U.S. patent application Ser. No. 13/392,615, filed on Feb. 27, 2012, which is a national stage filing under 35 U.S.C. § 371 of PCT/EP2010/062601, filed Aug. 30, 2010, which claims priority to European Patent Application No. 09176575.0, filed Nov. 20, 2009, and U.S. Provisional Patent Application No. 61/239,086, filed on Sep. 2, 2009, the contents of which are each incorporated herein by reference in their entirety.

FIELD OF THE INVENTION

The present invention generally relates to nitrogen containing surfactants as adjuvants that enhance the activity of agricultural formulations.

BACKGROUND OF THE INVENTION

The bioefficacy of pesticides is known to be enhanced by the addition of appropriate surfactants, or adjuvants. For example, it is well known that the bioefficacy of glyphosate, a herbicide, can be enhanced by tallowamine ethoxylate surfactant. However, some commonly used surfactants have unfavorable aquatic toxicity or eye irritation profiles. Examples of such surfactants are, tallowamine ethoxylate, $C_{14}$ alcohol ethoxylate (1-4 EO), and $C_{18}$ alkyl trimethyl quaternary surfactants. Many attempts have been tried to replace such surfactants with one having better aquatic toxicity or eye irritation profiles. Any improvement in terms of aquatic or eye irritation will be seen as a step forward in the right direction to protect the environment. However, it is well known to those skilled in the art that improvement in aquatic toxicity or eye irritation usually go in the opposite direction of improvement in bioefficacy. One example was that, in an attempt to replace the tallowamine ethoxylate in glyphosate, alkyl poly glucoside (APG) surfactant was introduced as a mild surfactant having as good an efficacy enhancing property as tallowamine ethoxylate but it was later proved that APG surfactants were actually weak in enhancing glyphosate bioefficacy. Until now there has not been found any surfactants which can enhance glyphosate efficacy as well as tallowamine ethoxylate does while at the same time have low aquatic toxicity and eye irritation profiles. Glyphosate is the largest volume pesticide in the world. Therefore, there is a need to find a suitable surfactant having good bioefficacy enhancing property, improved aquatic toxicity, and improved eye irritation profiles for general pesticide use, and particularly for glyphosate use.

U.S. Pat. No. 6,645,912 discloses a herbicide composition with a 2-nitrogen amidoamine di-C1-C4 alkyl amine oxide of the formula:

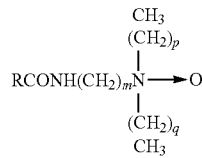

Where R is C6-C20, m=1-4, and p and q=0-3.

WO29082675A1 discloses a composition comprising an amidoamine alkoxylate of the formula:

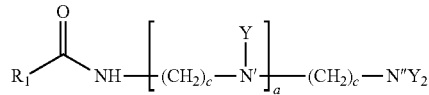

Wherein a=1-3; c=2-3; R1=C5 to C19 alkyl radical and wherein Y is each independently: H,

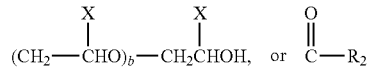

Wherein X is independently H, CH3, or C2H5, b=0-10, and R2 is C5-C19 radical. Where at least one of the N' and N" is oxidized or quaternized. However, this type of amidoamine, its oxide and quaternary compounds have been well known for many years.

WO2009080225A2 discloses an adjuvant composition for an agrochemical formulation comprising a salt of N-lauryl iminopropinoic acid and an alkylamine derivative with the general structure:

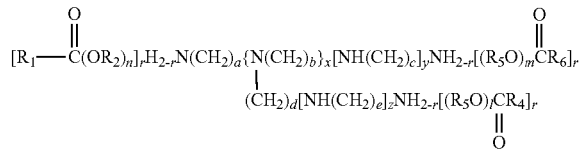

Wherein $R_1$, $R_4$, and $R_6$ each independently represents hydrogen or a $C_{1-30}$ alkyl or alkenyl group; $(OR_2)_n$, $(OR_3)_1$, and $(OR_5)_m$ each independently represents a random polyalkoxide group, a block polyalkoxide group, or a $C_{2-6}$ linear or branched, alkyl sulf(on)ate; $R_2$, $R_3$, and $R_5$ each independently represents a $C_{2-6}$ alkyl group; l, m, and n, each independently represents a number from 1 to 100, r represents a number from 1 to 2; a, b, c, d, and e each independently represents a number from 1 to 12; and each of x, y, and z independently represent a number from 1 to 100.

The alkylamine derivatives suitable for the adjuvant compositions according to the document include, but not limited to: monoethanolamine, diethanolamine, triethanolamine, and a polyaliphatic amine and/or its derivatives. It is claimed that the composition has reduced eye and skin irritation but no actual data is disclosed. It is also claimed that the composition provided weed control equal to the standard Roundup® Ultra using three examples of 360 g/l IPA-glyphosate formulations.

This document does not disclose whether or not the salt of N-lauryl iminopropinoic acid is effective when used alone in glyphosate formulations. Without proper testing of individual surfactants, it is not possible to determine whether the effect seen in the mixture of three surfactants comes from the claimed surfactant or the other two surfactants. Moreover, no actual bioefficacy data and especially no data are provided on the degree of "overall kill" provided in the absence of surfactants and in the presence of surfactants; without such data it is not possible to determine whether or not the claimed alkyl amido betaine was effective in enhancing herbicidal activity of glyphosate under the conditions of the test reported. Moreover, it does not disclose whether or not the salt of N-lauryl iminopropinoic acid is compatible in other salts of glyphosate such as high load ammonium and potassium glyphosate formulations.

WO2000038523 (Huntsman, U.S. Pat. No. 6,500,784, U.S. Pat. No. 6,653,257, EP1139761) discloses an amphoteric surfactant with the structure $RCONH(CH2)_nN^+R^1{}_2CH_2COO^-$ where $R^1$ is alkyl or hydroxyl alkyl group with C1 to C4 and n=2-4, and discloses a betaine with the structure $R\ R^1{}_2N^+CH_2COO^-$ where $R^1$ is alkyl or hydroxyl alkyl group with C1 to C4. The amphoterics disclosed there mainly functioned as a co-surfactant to solubilize a ether carboxylate in to concentrated glyphosate systems. In the context of the document, there was no mention of bioefficacy of betaines or other amphoteric surfactants by themselves. Only in examples 29-53 a mixture of three surfactants (not betaine alone) was mentioned to exhibit an improved wetting and bioefficacy. However, without proper testing of individual surfactant, it is not possible to determine whether the effect seen in the mixture of three surfactants comes from the claimed surfactant or the other two surfactants. Moreover, no actual bioefficacy data and especially no data are provided on the degree of "overall kill" provided in the absence of surfactants and in the presence of surfactants; without such data it is not possible to determine whether or not the claimed alkyl amido betaine was effective in enhancing herbicidal activity of glyphosate under the conditions of the test reported. This patent requires Na ion to be <0.035% for the glyphosate formulation to be stable. Moreover, it used only IPA-glyphosate as examples. It is only recently known that many soluble surfactants in IPA-glyphosate are not soluble in concentrated K or NH4 glyphosate formulations. Our tests indicated that a composition of 51.3% potassium glyphosate, an un-saturated glyphosate salt aqueous solution, could not even dissolve 1.8% stearyl dimethylamidopropyl betaine. Since stearyl dimethylamidopropyl betaine itself had poor solubility in concentrated potassium glyphosate system, it is expected that the solubility of stearyl dimethylamidopropyl betaine plus ether carboxylate would be even worst in the concentrated potassium glyphosate system. Therefore, the claimed formulation in claim 1 in the document may not be stable, that is not useful, in a concentrated K glyphosate system.

US2004/0224846A1 (U.S. Pat. No. 6,992,046B2) claims a glyphosate formulation with a trialkyl betaine (or trialkyl amido propyl betaine) plus at least one alkylamine alkoxylate. No data are provided on the degree of "overall kill" provided in the absence of surfactants and in the presence of surfactants; without such data it is not possible to determine whether or not the mixture of trialkyl betaine (or trialkyl amido propyl betaine) and alkylamine alkoxylate was effective in enhancing herbicidal activity of glyphosate under the conditions of the test reported. Moreover, since alkylamine alkoxylate alone is effective in enhancing glyphosate efficacy, it is not possible to tell from the context of the document whether or not the effect cited in the document was from the alkylamine alkoxylate, the betaine, or combination of both.

US 20050170965(A1) (Rhodia) (WO 03/063589 A2, EP1469731A2, US2003/0158042, US2004/0224846, EP2025230) discloses a betaine with following structures and at least one more surfactant which includes alkylamine ethoxylate.

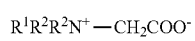
(I)

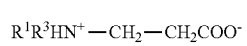
(II)

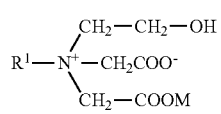
(III)

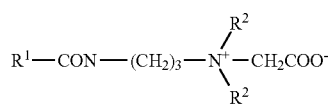
(IV)

Where $R^2$ is alkyl, and $R^3$ is hydrogen, alkyl or —CH$_2$—COOM.

In the context of the document, no data are provided on the degree of "overall kill" provided in the absence of surfactants and in the presence of surfactants; without such data it is not possible to determine whether or not the mixture of trialkyl betaine (or trialkyl amido propyl betaine) and alkylamine alkoxylate was effective in enhancing herbicidal activity of glyphosate under the conditions of the test reported. Moreover, since alkylamine alkoxylate alone is effective in enhancing glyphosate efficacy, it is not possible to tell from the context of the document whether or not the claimed effect was from the alkylamine alkoxylate, the betaine, or combination of both.

The document also indicates the aqueous glyphosate formulation is stable on storage. However, it is only recently known that many stable surfactants in IPA-glyphosate are not soluble in concentrated K or NH4 glyphosate formulations. Tests indicate that a composition of 360 g ae/l di-ammonium glyphosate could not dissolve 5.4% coco dimethyl betaine and a composition of 480 g ae/l potassium glyphosate could not dissolve 5.4% coco dimethylamidopropyl betaine. Since coco dimethyl betaine and coco dimethylamidopropyl betaine had poor solubility in concentrated potassium and di-ammonium glyphosate systems, it is expected that the claimed formulation in claim 16 of the document may not be stable in concentrated K or NH4 glyphosate systems.

US20080312083 (Rhodia PTC filed in 2005) discloses glyphosate with a betaine of the structure $R^1R^2R^2N^+$—CH$_2$COO$^-$ (I) or $R^1$—CO—NH—$R^4$—$R^2R^2N^+$—CH$_2$COO$^-$ where $R^1$ is C3-C30 and $R^2$ is C1-C3. A herbicidal aqueous composition is illustrated, comprising: (i) at least 360 g/L of an aminophosphate or aminophosphonate salt; (ii) at least 80 g/L of a surfactant system which comprises: a betaine surfactant composition comprising: water, a betaine having the formula $R^1R^2R^2N^+$—CH$_2$COO$^-$, wherein: $R^1$ is a linear or branched hydrocarbon radical having 3 to 30 alkoxide units the radicals $R^2$, which may be identical or different, are each a $C_1$-$C_3$ alkyl radical, at least 1% by weight of a chloride salt, and (iii) optionally, at least one surfactant other than the betaine of the betaine surfactant composition. The document states that the examples show that the composition according to the invention have a surprising good stability, without crystals formation. Meanwhile the compositions according to the examples have a better (lower fresh weight) and/or quicker bio-efficacy (higher brownout) on at least some significant weeds (annual ryegrass and wild radish). No data are provided on the degree of "overall kill" provided in the absence of surfactant and in the presence of surfactants; without such data it is not possible to determine whether or not the trialkyl betaine (or trialkyl amido propyl betaine) was effective in enhancing herbicidal activity of glyphosate under the conditions of the test reported. The document states that the examples show that the composition according to the invention have a surprising good stability, without crystals formation. Tests indicate that a composition of 360 g ae/l potassium glyphosate could not dissolve 80 g/l coco dimethylamidopropyl betaine.

WO2008066611 (Rhodia, Canadian patent 2629862) claims an surfactant blend of surfactants selected from any two of the groups: (1) alkylpolyglucoside, (2) phosphate ester, (3) sulfonate, sulfonsuccinate, alkyl ether carbonxylate, alkoxylated fatty acid, alkoxylated alcohol, and (4) imidazoline based surfactant or a aminopropionate based surfactant. No biological data is shown.

Eco toxicity of a chemical is classified according to the Directive 91/325/EEC [2] as well as 1999/45/EC. Limits are specified for the application of risk phrases and the "N" symbol (sometimes shown as dead-fish-dead-tree symbol). Possible combinations are as follows:

| Symbol | Risk phrase |
| --- | --- |
| N | R 50/53 |
| N | R 50 |
| N | R 51/53 |
| — | R 52/53 |
| — | R 52 |
| — | R 53 |

The risk phrases have the following meaning:
R 50: Very toxic to aquatic organisms
R 51: Toxic to aquatic organisms
R 52: Harmful to aquatic organisms
R 53: May cause long term adverse effects in the aquatic environment Some of the objectives of the present invention are as follows:
(1) use a low toxicity surfactant of the present invention in agricultural formulations that do not carry a "dead-fish-dead-tree" symbol; (2) use a low toxicity surfactant of the present invention in agricultural formulations that not only do not carry a "dead-fish-dead-tree" symbol but also have low fish toxicity; (3) use a low toxicity surfactant of the present invention in agricultural formulations that not only do not carry a "dead-fish-dead-tree" symbol but also have low fish and low daphnia toxicity; (4) use a low toxicity surfactant of the present invention in agricultural formulations that not only do not carry a "dead-fish-dead-tree" symbol but also have low fish, low daphnia, and low algae toxicity; (5) provide a concentrated and stable liquid glyphosate formulation (equal or greater than 360 g ae/l) comprising the surfactant of the present invention without a need for a compatibility agent; (6) provide a concentrated and stable liquid glyphosate formulation (equal or greater than 360 g ae/l) comprising the surfactant of the present invention with C5-12 dimethylamidopropylamine as the compatibility agent; and (7) provide a formulation with improved bioefficacy, compared to the same formulation without surfactant.

SUMMARY OF THE INVENTION

The present invention generally relates to nitrogen containing surfactants with a $N^+$—$CH_2COO^-$, $N^+$—$CH_2COOCH_3$, $N$—$CH_2COO^-M^+$, $N$—$CH_2CH_2COO^-M^+$, or amine oxide functionality which enhance the efficacy of agricultural formulations. Some of the surfactants of the present invention are compatible in high load ammonium and potassium glyphosate formulations with or without a compatibility agent.

In one embodiment, the present invention is a surfactant useful for enhancing the efficacy of agricultural formulations comprising the following general structure:

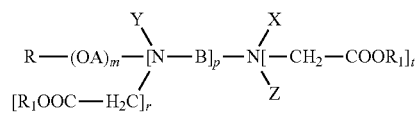

Where R is C6-C22 linear or branched, saturated or non-saturated hydrocarbon group; A=C1-C3 linear or branched alkyl; m=0-10; B=C2-C6 alkyl; p=0-5; r=0-1; t=0-1; $R_1$ is nothing, hydrogen or $CH_3$ and the whole molecule has a chloride as the counter ion for each hydrogen or $CH_3$ when $R_1$ is hydrogen or $CH_3$; X and Y independently are nothing (or a pair electron), H (hydrogen), $CH_3$ (methyl), a polyalkoxide group with 1 to 20 alkoxide units, $CH_2COO$, $CH_2COO^-M^+$ or $CH_2CH_2COO^-M^+$ where M is H, Na, K, Li, NH4, monoethanolamine, diethanolamine, triethanolamine, isopropylamine, dimethylamine, or dimethylamidopropylamine (DMAPA); Z is H (hydrogen), C1-C18 linear or branched, saturated or unsaturated alkyl group, a polyalkoxide group with 1 to 20 alkoxide units, $CH_2COO$, $CH_2COO^-M^+$ or $CH_2CH_2COO^-M^+$ where M is H, Na, K, Li, NH4, monoethanolamine, diethanolamine, triethanolamine, isopropylamine, dimethylamine, or dimethylamidopropylamine (DMAPA); with the provisos that (1) the said surfactant has at least one N—$CH_2COO$, N—$CH_2COO^-M^+$, or N—$CH_2CH_2COO^-M^+$ group where M is H, Na, K, Li, NH4, monoethanolamine, diethanolamine, triethanolamine, isopropylamine, dimethylamine, or dimethylamidopropylamine (DMAPA) and (2) when m=p=0 and t=1, X and Z are not a methyl group at the same time.

In another embodiment, the present invention is a surfactant useful for enhancing the efficacy of agricultural formulations comprising the following general structure:

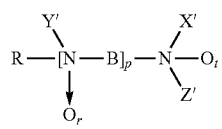

Where R is C6-C22 linear or branched, saturated or non-saturated hydrocarbon group; B=C2-C6 alkyl; p=0-5; r=0-1; t=0-1; X', Y', and Z' independently are $CH_3$ (methyl) or a polyalkoxide group with 1 to 20 alkoxide units; with the provisos that (1) the said surfactant has at least one amide oxide group and (2) when p=0 and t=1, X' and Z' are not a methyl group at the same time.

In a further embodiment the present invention is a surfactant useful for enhancing the efficacy of agricultural formulations comprising the following general structure:

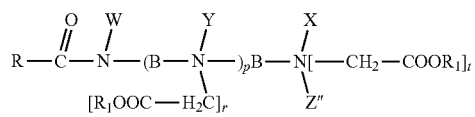

Where R is C6-C22 linear or branched, saturated or non-saturated hydrocarbon group; B=C2-C6 alkyl; p=0-5; r=0-1; t=0-1; W is H, $CH_2COO$, or $CH_2CH_2OH$; $R_1$ is nothing, hydrogen or $CH_3$ and the whole molecule has a chloride as the counter ion for each hydrogen or $CH_3$ when $R_1$ is hydrogen or $CH_3$; X, Y and Z" independently are nothing (or a pair electron), H (hydrogen), $CH_3$ (methyl), a polyalkoxide group with 1 to 20 alkoxide units, $CH_2COO$, $CH_2COO^-M^+$ or $CH_2CH_2COO^-M^+$ where M is H, Na, K, Li, NH4, monoethanolamine, diethanolamine, triethanolamine, isopropylamine, dimethylamine, or dimethylamidopropylamine (DMAPA); Z is H (hydrogen), C1-C18 linear or branched, saturated or unsaturated alkyl group, a polyalkoxide group with 1 to 20 alkoxide units, $CH_2COO$, $CH_2COO^-M^+$ or $CH_2CH_2COO^-M^+$ where M is H, Na, K, Li, NH4, monoethanolamine, diethanolamine, triethanolamine, isopropylamine, dimethylamine, or dimethylamidopropylamine (DMAPA); with the provisos that (1) the said surfactant has at least one $N—CH_2COO$, $N—CH_2COO^-M^+$, or $N—CH_2CH_2COO^-M^+$ group where M is H, Na, K, Li, NH4, monoethanolamine, diethanolamine, triethanolamine, isopropylamine, dimethylamine, or dimethylamidopropylamine (DMAPA) and (2) when p=0 and t=1, X and Z" are not a alkyl group or a hydroxyalkyl group at the same time.

In yet another embodiment the present invention comprises a surfactant useful for enhancing the efficacy of agricultural formulations comprising the following general structure:

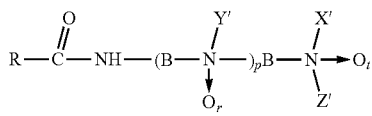

Where R is C6-C22 linear or branched, saturated or non-saturated hydrocarbon group; B=C2-C6 alkyl; p=0-5; r=0-1; t=0-1; X', Y', and Z' independently are $CH_3$ (methyl) or a polyalkoxide group with 1 to 20 alkoxide units; with the provisos that (1) the said surfactant has at least one amine oxide group; and (2) when p=0, and t=1, X' and Z' are not a C1-C4 alkyl group at the same time.

Other embodiments of the invention include formulations comprising at least one of the nitrogen containing surfactants combined with a pesticide that may be one or more of a herbicide, a fungicide, or insecticide.

DETAILED DESCRIPTION OF THE INVENTION

Figure 1:
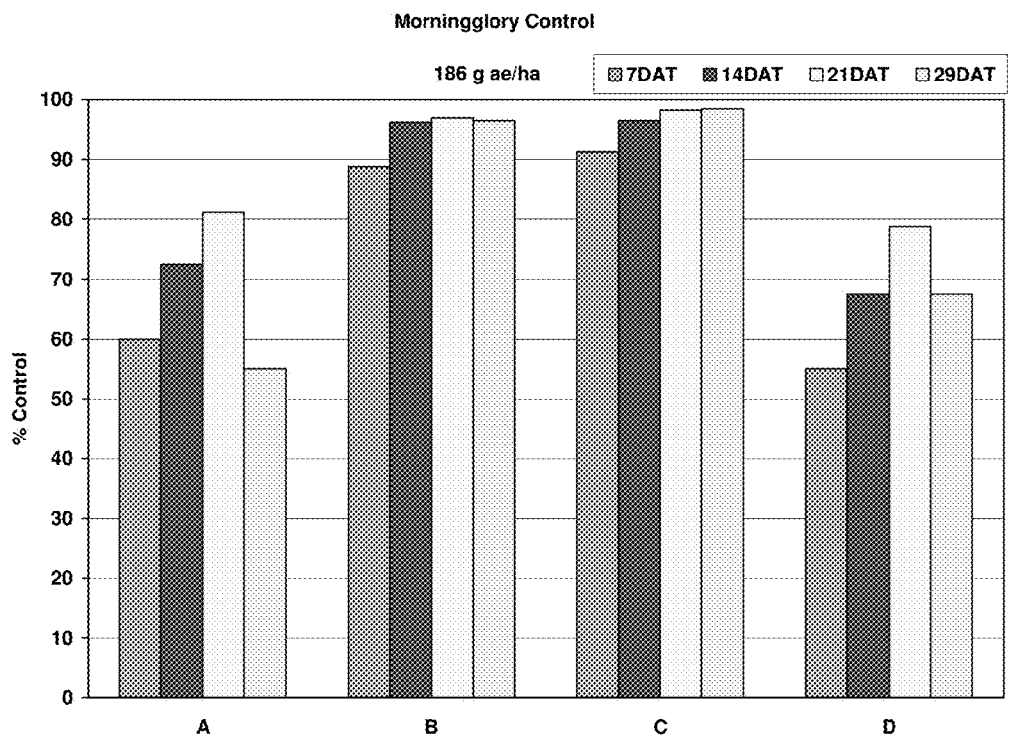
FIG. 1 is a bar graph illustrating the % control results of applying the glyphosate samples of Table 1 at 186 g ae/ha to morning glory at 7, 14, 21 and 29 days after treatment.
Figure 2:
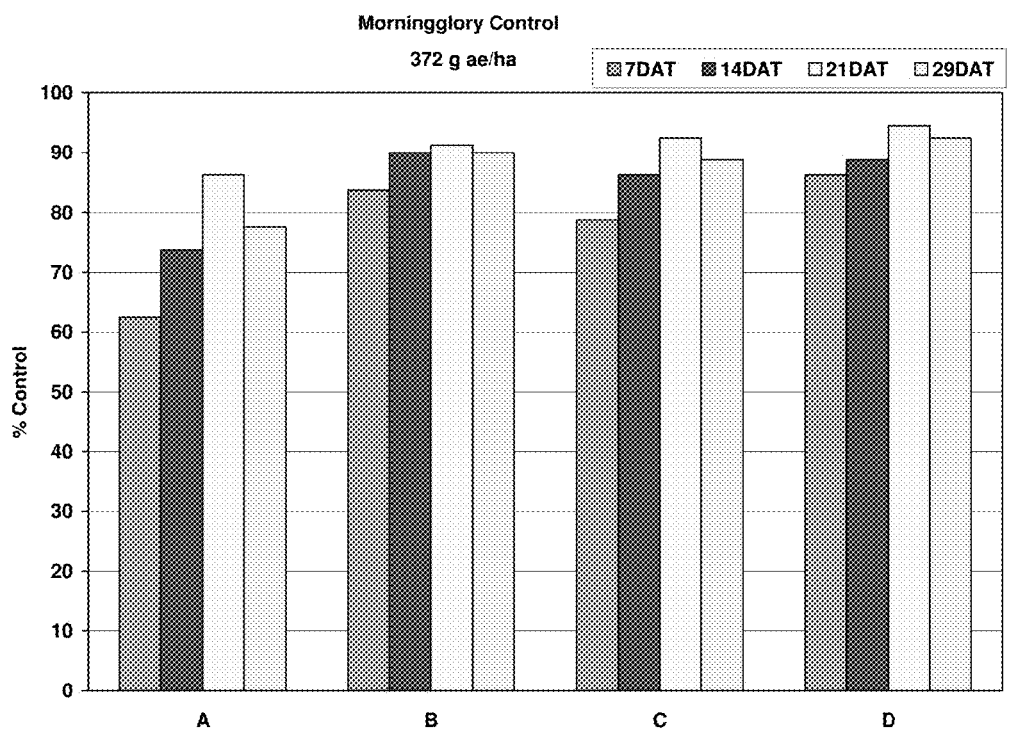
FIG. 2 is a bar graph illustrating the % control results of applying the glyphosate samples of Table 1 at 372 g ae/ha to morning glory at 7, 14, 21 and 29 days after treatment.
Figure 3:
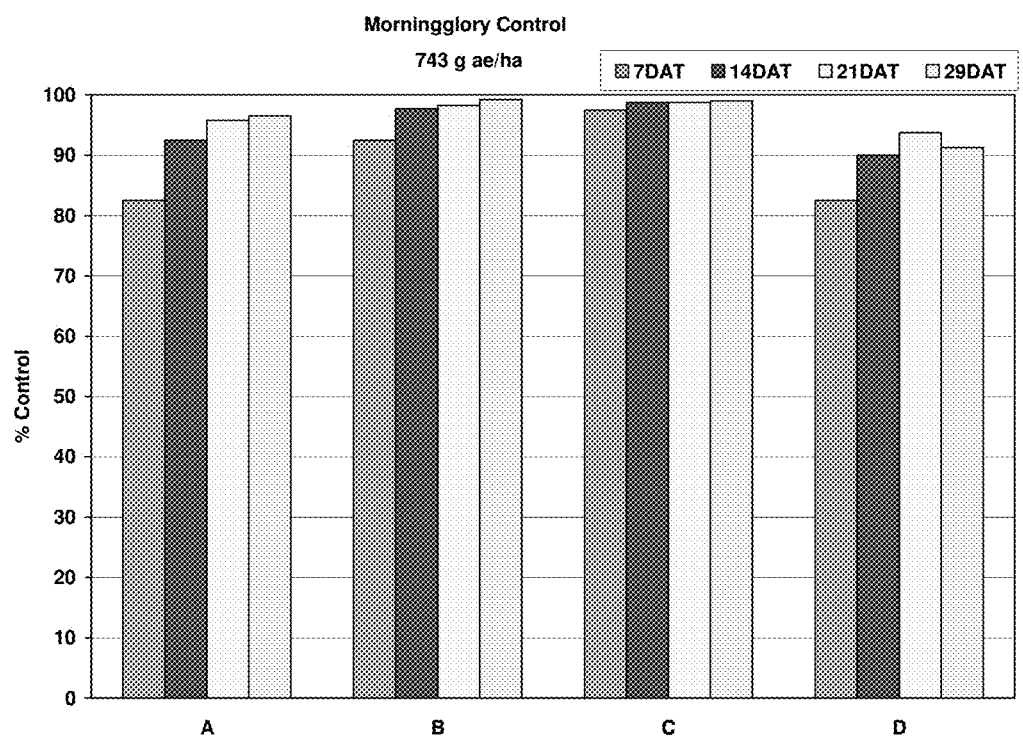
FIG. 3 is a bar graph illustrating the % control results of applying the glyphosate samples of Table 1 at 743 g ae/ha to morning glory at 7, 14, 21 and 29 days after treatment.
Figure 4:
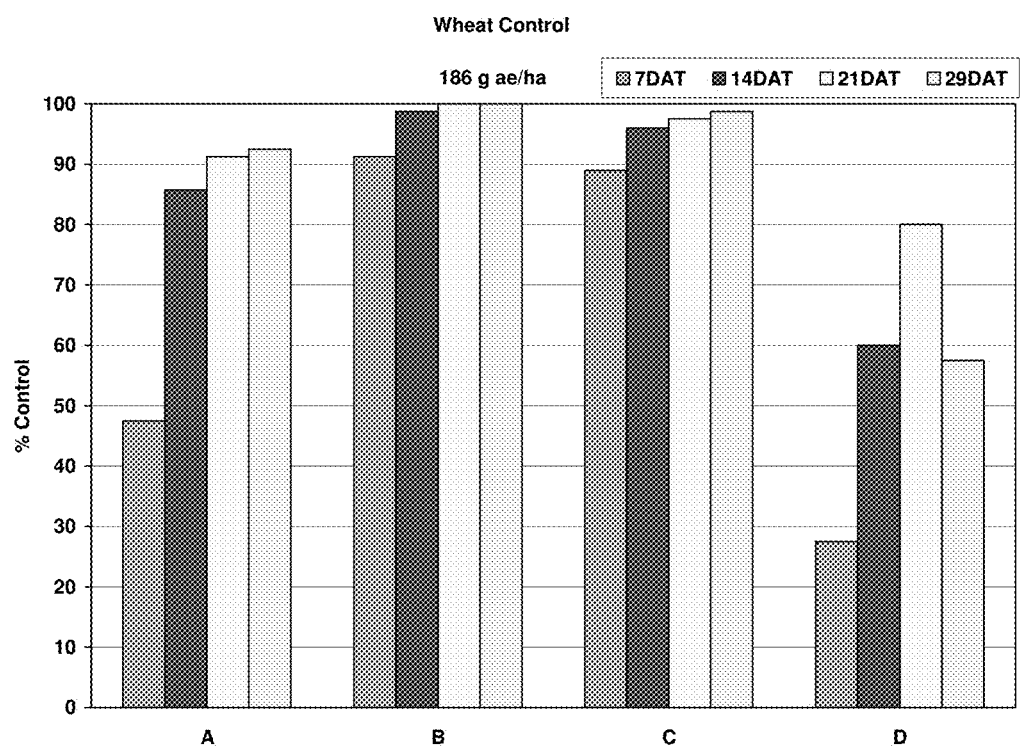
FIG. 4 is a bar graph illustrating the % control results of applying the glyphosate samples of Table 1 at 186 g ae/ha to wheat at 7, 14, 21 and 29 days after treatment.
Figure 5:
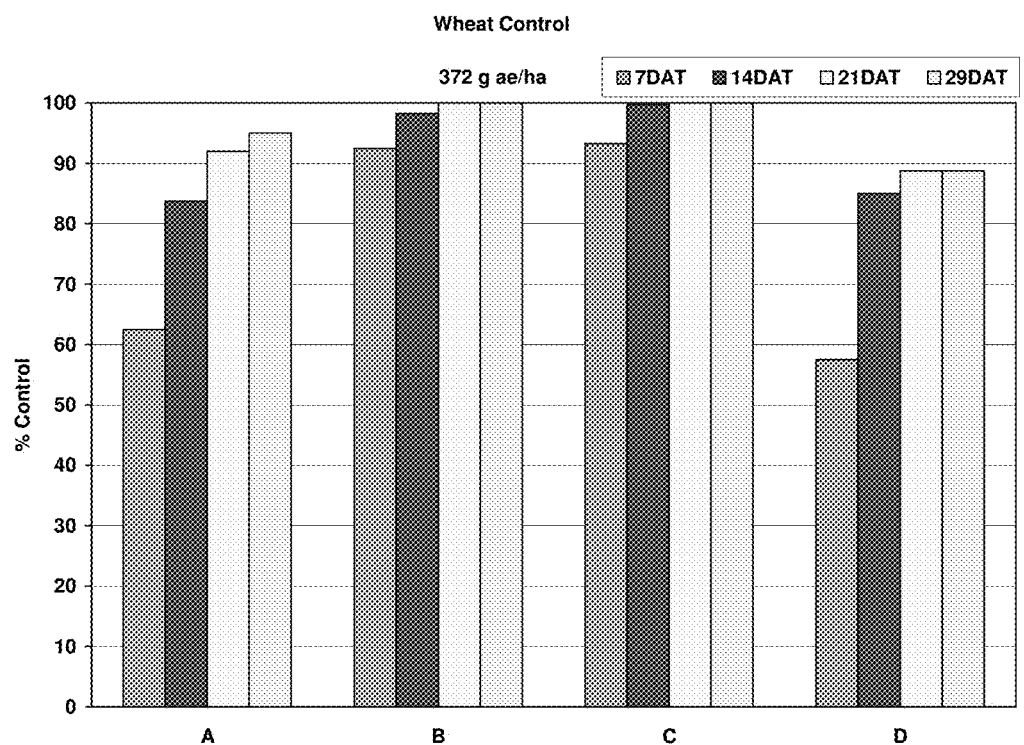
FIG. 5 is a bar graph illustrating the % control results of applying the glyphosate samples of Table 1 at 372 g ae/ha to wheat at 7, 14, 21 and 29 days after treatment.
Figure 6:
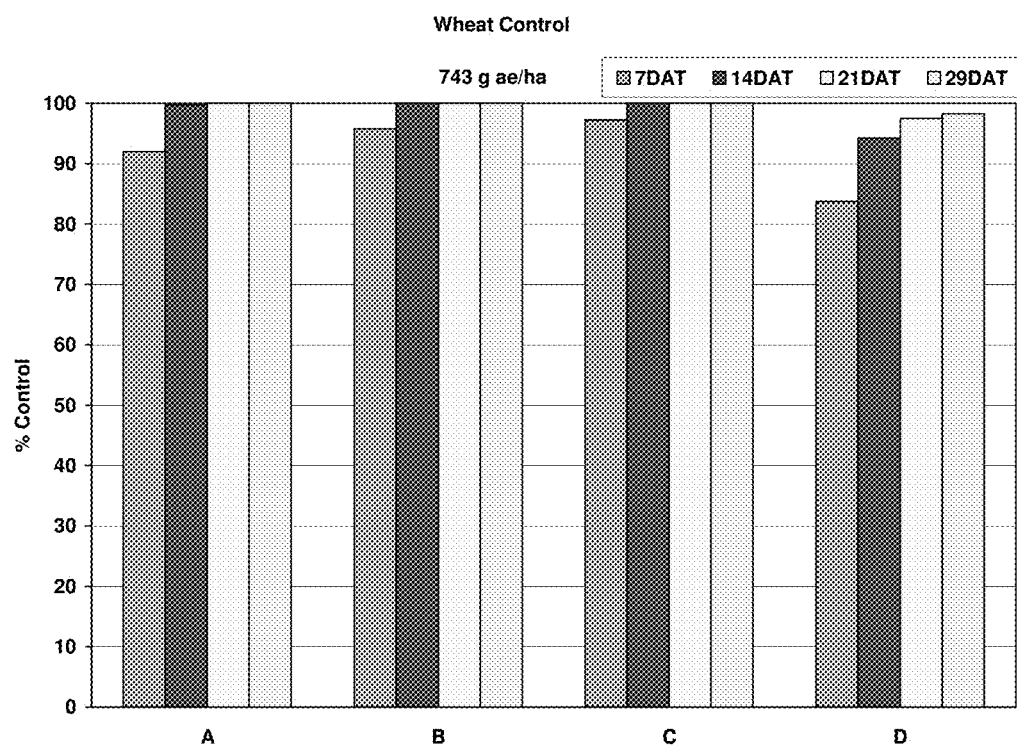
FIG. 6 is a bar graph illustrating the % control results of applying the glyphosate samples of Table 1 at 743 g ae/ha to wheat at 7, 14, 21 and 29 days after treatment.

There is a need to have a low toxicity surfactant which can enhance the efficacy of a agricultural formulation when used alone. The ability of one single surfactant to offer enhanced efficacy to an agricultural formulation is more practical because the surfactant has the flexibility of being used alone or used with other surfactants for synergistic effect.

The following nitrogen containing surfactants with a $N^+—CH_2COO^-$, $N^+—CH_2COOCH_3$, $N—CH_2COO^-M^+$, $N—CH_2CH_2COO^-M^+$, or amine oxide functionality are useful to enhance the efficacy of an agricultural chemical. One or more of the following surfactants can be used in agricultural formulations.

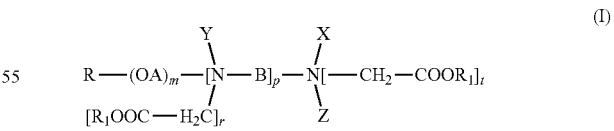

Where R is C6-C22 linear or branched, saturated or non-saturated hydrocarbon group; A=C1-C3 linear or branched alkyl; m=0-10; B=C2-C6 alkyl; p=0-5; r=0-1; t=0-1; $R_1$ is nothing, hydrogen or $CH_3$ and the whole molecule has a chloride as the counter ion for each hydrogen or $CH_3$ when $R_1$ is hydrogen or $CH_3$; X and Y independently are nothing (or a pair electron), H (hydrogen), $CH_3$ (methyl), a polyalkoxide group with 1 to 20 alkoxide units, $CH_2COO$, $CH_2COO^-M^+$ or $CH_2CH_2COO^-M^+$ where M is H, Na, K, Li, NH4, monoethanolamine, diethanolamine, triethanolamine, isopropylamine, dimethylamine, or dimethylamidopropylamine (DMAPA); Z is H (hydrogen), C1-C18 linear or branched, saturated or unsaturated alkyl group, a polyalkoxide group with 1 to 20 alkoxide units, $CH_2COO$, $CH_2COO^-M^+$ or $CH_2CH_2COO^-M^+$ where M is H, Na, K, Li, NH4, monoethanolamine, diethanolamine, triethanolamine, isopropylamine, dimethylamine, or dimethylamidopropylamine (DMAPA); with the provisos that (1) the said surfactant has at least one $N-CH_2COO$, $N-CH_2COO^-M^+$, or $N-CH_2CH_2COO^-M^+$ group where M is H, Na, K, Li, NH4, monoethanolamine, diethanolamine, triethanolamine, isopropylamine, dimethylamine, or dimethylamidopropylamine (DMAPA) and (2) when m=p=0 and t=1, X and Z are not a methyl group at the same time.

It shall be pointed out that the conventional representation of a betaine functionality is $N^+-CH_2COO^-$. However, in the betaine structures through out the specification, the positive charge on the nitrogen and negative charge on $CH_2COO$ is omitted.

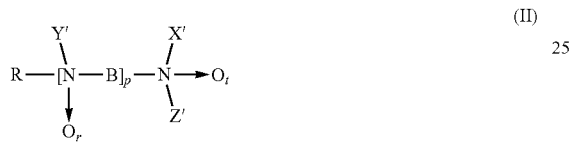

(II)

Where R is C6-C22 linear or branched, saturated or non-saturated hydrocarbon group; B=C2-C6 alkyl; p=0-5; r=0-1; t=0-1; X', Y', and Z' independently are $CH_3$ (methyl) or a polyalkoxide group with 1 to 20 alkoxide units; with the provisos that (1) the said surfactant has at least one amide oxide group and (2) when p=0 and t=1, X' and Z' are not a methyl group at the same time.

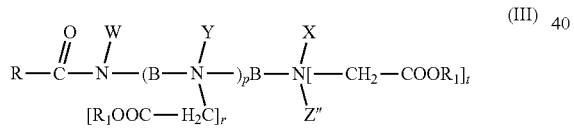

(III)

Where R is C6-C22 linear or branched, saturated or non-saturated hydrocarbon group; B=C2-C6 alkyl; p=0-5; r=0-1; t=0-1; W is H, $CH_2COO$, or $CH_2CH_2OH$; $R_1$ is nothing, hydrogen or $CH_3$ and the whole molecule has a chloride as the counter ion for each hydrogen or $CH_3$ when $R_1$ is hydrogen or $CH_3$; X, Y and Z" independently are nothing (or a pair electron), H (hydrogen), $CH_3$ (methyl), a polyalkoxide group with 1 to 20 alkoxide units, $CH_2COO$, $CH_2COO^-M^+$ or $CH_2CH_2COO^-M^+$ where M is H, Na, K, Li, NH4, monoethanolamine, diethanolamine, triethanolamine, isopropylamine, dimethylamine, or dimethylamidopropylamine (DMAPA); Z is H (hydrogen), C1-C18 linear or branched, saturated or unsaturated alkyl group, a polyalkoxide group with 1 to 20 alkoxide units, $CH_2COO$, $CH_2COO^-M^+$ or $CH_2CH_2COO^-M^+$ where M is H, Na, K, Li, NH4, monoethanolamine, diethanolamine, triethanolamine, isopropylamine, dimethylamine, or dimethylamidopropylamine (DMAPA); with the provisos that (1) the said surfactant has at least one $N-CH_2COO$, $N-CH_2COO^-M^+$, or $N-CH_2CH_2COO^-M^+$ group where M is H, Na, K, Li, NH4, monoethanolamine, diethanolamine, triethanolamine, isopropylamine, dimethylamine, or dimethylamidopropylamine (DMAPA) and (2) when p=0 and t=1, X and Z" are not a alkyl group or a hydroxyalkyl group at the same time.

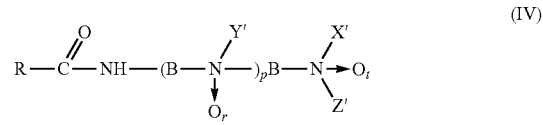

(IV)

Where R is C6-C22 linear or branched, saturated or non-saturated hydrocarbon group; B=C2-C6 alkyl; p=0-5; r=0-1; t=0-1; X', Y', and Z' independently are $CH_3$ (methyl) or a polyalkoxide group with 1 to 20 alkoxide units; with the provisos that (1) the said surfactant has at least one amide oxide group; and (2) when p=0, and t=1, X' and Z' are not a C1-C4 alkyl group at the same time.

The following structures (1)-(6) are preferred structures of the present invention. R, X, Y, Z, M, p, m, r and t have the same definition as in structure (I) if not specified.

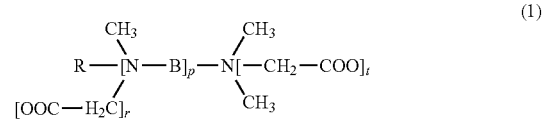

(1)

Where p>0.

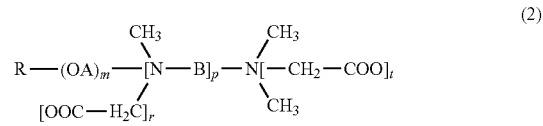

(2)

(3)

(4)

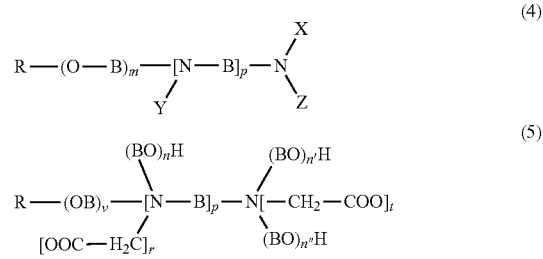

(5)

Where n=0-100, n'=0-100, n"=0-100, when p=0 and v=0, n' and n" can't be 1 at the same time.

(6)

The following structure (a)-(d) are some of the more preferred surfactants. R, X, Y, Z, M, p, m, r and t have the same definition as in structure (I) if not specifically mentioned.

(a)
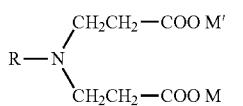

Where R is lauryl or coco.

(b)
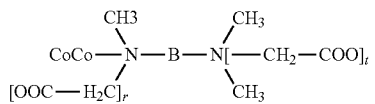

Where B is ethylene, propylene, or isopropylene group. r=0-1, t=0-1, r and t can't be both zero at the same time.

(c)
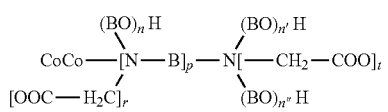

Where p=0-2. B is ethylene, propylene, or isopropylene group. n=1-20, n'=1-20, n"=1-20, r=0-1, t=0-1; with the provisos that r and t can't be both zero at the same time, that p and t can't be both zero at the same time and that when p=0, n and n' can't be 1 at the same time and said surfactant comprises a betaine of ethoxylated cocoamine.

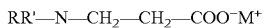 (d)

Where, R is tallow and R' is C8.

In certain preferred embodiments, the above surfactant is used together with C5-C12 (particularly C6-C9) dimethyl amidopropylamine, One embodiment of the present invention is a herbicide formulation containing the surfactants of the present invention. Suitable herbicides include acetochlor, acifluorfen, aclonifen, alachlor, ametryn, amidosulfuron, aminopyralid, amitrole, anilofos, asulam, atrazine, azafenidin, azimsulfuron, benazolin, benfluralin, bensulfuron-methyl, bentazone, bifenox, binalafos, bispyribac-sodium, bromacil, bromoxynil, butachlor, butroxidim, cafenstrole, carbetamide, carfentrazone-ethyl, chloridazon, Chlorimuron-ethyl, chlorobromuron, chlorotoluron, chlorsulfuron, cinidon-ethyl, cinosulfuron, clethodim, Clomazone, Clopyralid, Cloransulam-methyl, Clorsulfuron, Cyanazine, Cycloate, Cyclosulfamuron, Cycloxydim, Dalapon, Desmedipham, Dicamba, Dichlobenil, Dichlormid, Diclosulam, Diflufenican, Dimefuron, Dimepipeate, Dimethachlor, Dimethenamid, Diquat, Diuron, Esprocarb, Ethalfluralin, Ethametsulfuron-methyl, Ethofumesate, Ethoxysulfuron, Fentrazamide, Flazasulfuron, Florasulam, Fluchloralin, Flufenacet, Flumetsulam, Flumioxazin, Fluometuron, Flupyrsulfuron-methyl, Fluro-chloridone, Fluroxypyr, Flurtamone, Fomesafen, Foramsulfuron, Glufosinate, Hexazinone, Imazamethabenz-m, Imazamox, mazapic, Imazapyr, Imazaquin, Imazethapyr, Imazosulfuron, Iodosulfuron, Ioxynil, Isoproturon, Isoxaben, Isoxaflutole, Lactofen, Lenacil, Linuron, Mefenacet, Mesosulfuron-Methyl, Mesotrione, Metamitron, Metazachlor, Methabenzthiazuron, Metobromuron, Metolachlor, Metosulam, Metoxuron, Metribuzin, Metsulfuron-methyl, Molinate, MSMA, Napropamide, Nicosulfuron, Norflurazon, Oryzalin, Oxadiargyl, Oxadiazon, Oxasulfuron, Oxyfluorfen, Paraquat, Pendimethalin, Phenmedipham, Picloram, Pretilachlor, Profoxydim, Prometryn, Propanil, Propisochlor, Propoxycarbazone, Propyzamide, Prosulfocarb, Prosulfuron, Pyraflufen-ethyl, Pyrazosulfuron, Pyridate, Pyrithiobac, Quinclorac, Quinmerac, Rimsulfuron, Sethoxydim, Simazine, S-Metolachlor, Sulcotrione, Sulfentrazone, Sulfosulfuron, Tebuthiuron, Tepraloxydim, Terbuthylazine, Terbutryn, Thifensulfuron-methyl, Thiobencarb, Tralkoxydim, Tri-allate, Triasulfuron, Tribenuron-methyl, Triclopyr, Trifloxysulfuron, Trifluralin, Triflusulfuron-methyl, Tritosulfuron, and mixtures and combinations thereof. Preferred herbicides are Acetochlor, Atrazine, Dicamba, Glufosinate, Paraquat, glyphosate, 2,4-D and mixtures and combinations thereof. More preferred herbicides are 2,4-D, Atrazine, Dicamba, glyphosate, and Glufosinate and mixtures and combinations thereof. The most preferred herbicide is glyphosate. When the herbicide is an acid, it can be used in the acid form though it is preferred that the herbicide be in the salt form selected from at least one of the group of an amine, lithium, sodium, ammonium or potassium. It shall be pointed out that when a pesticide appears in the text as a general name without specifying the counterions, it means both its acid form and salt form through out the specification.

Preferred herbicides are glyphosate, dicamba, 2,4-D, glufosinate, and atrazine.

Another embodiment of the present invention is a fungicide formulation containing the surfactants of the present invention. Examples of suitable fungicides are: Acibenzolar-S-methyl, aldimorph, amisulbrom, anilazine, azaconazole, azoxystrobin, benalaxyl, benodanil, benomyl, benthiavalicarb, binapacryl, biphenyl, bitertanol, blasticidin-S, boscalid, bromuconazole, bupirimate, captafol, captan, carbendazim, carboxin, carpropamid, chloroneb, chlorothalonil, chlozolinate, copper, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, dinocap, dithianon, dodemorph, dodine, edifenphos, enestrobin, epoxiconazole, etaconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fentin acetate, fentin chloride, fentin hydroxide, ferbam, ferimzone, fluazinam, fludioxonil, flumorph, fluopicolide, fluoxastrobin, fluquinconazole, flusilazole, flusulfamide, flutolanil, flutriafol, folpet, fosetyl-Al, fthalide, fuberidazole, furalaxyl, furametpyr, guazatine, hexaconazole, hymexazole, imazalil, imibenconazole, iminoctadine, iodocarb, ipconazole, iprobenfos (IBP), iprodione, iprovalicarb, isoprothiolane, isotianil, kasugamycin, kresoxim-methyl, laminarin, mancozeb, mandipropamid, maneb, material of biological, mepanipyrim, mepronil, meptyldinocap, metalaxyl, metalaxyl-M, metconazole, methasulfocarb, metiram, metominostrobin, metrafenone, mineral oils, organic oils, myclobutanil, naftifine, nuarimol, octhilinone, ofurace, origin, orysastrobin, oxadixyl, oxolinic acid, oxpoconazole, oxycarboxin, oxytetracycline, pefurazoate, penconazole, pencycuron, penthiopyrad, phosphorous acid and, picoxystrobin, piperalin, polyoxin, potassium bicarbonate, probenazole, prochloraz, procymidone, propamocarb, propiconazole, propineb, proquinazid, prothiocarb, prothioconazole, pyraclostrobin, pyrazophos, pyribencarb, pyributicarb, pyrifenox, pyrimethanil, pyroquilon, quinoxyfen, quintozene (PCNB), salts, silthiofam, simeconazole, spiroxamine, streptomycin, sulphur, tebuconazole, teclofthalam, tecnazene (TCNB), terbinafine, tetraconazole, thiabendazole, thifluzamide, thiophanate, thiophanate-methyl, thiram, tiadinil, tolclofosmethyl, tolylfluanid, triadimefon, triadimenol, triazoxide, tricyclazole, tridemorph, trifloxystrobin, triflumizole, triforine, triticonazole, validamycin, valiphenal, vinclozolin, zineb, ziram, and zoxamide, and mixtures and combinations thereof Still another embodiment of the present invention is an insecticide formulation containing the surfactants of the present invention. Examples of suitable insecticides are: kerosene or borax, botanicals or natural organic compounds (nicotine, pyrethrin, strychnine and rotenone), chlorinated hydrocarbon (DDT, lindane, chlordane), organophosphates (malathion and diazinon), carbamates (carbaryl and propoxur), fumigants (naphthalene) and benzene (mothballs), synthetic pyrethroids, and mixtures and combinations thereof.

Yet still another embodiment of the present invention is a mixture of any herbicide, fungicide, and insecticide selected form the above groups containing the surfactants of the present invention.

Coco amphoacetate, lauryl amine oxide, lauryl dimethylbetaine, and coco dimethyl amidopropyl betaine surfactants are considered to be readily biodegradable, mild to skin, eyes, and aquatic life when compared to alkylamine ethoxylate. They are used widely in tear fee shampoos for babies. It is expected that the surfactants with the structures of the present invention can also be made mild.

The surfactants of the present invention can be used as a tank-mix additive or formulated in an in-can formulation. They are suitable in a solid pesticide formulation and, particularly, in a liquid pesticide formulation.

Other additives can be present in the formulations containing the surfactants of the present invention. They are defoamer, diluents, compatibility agents, biocides, thickeners, drift control agents, dyes, fragrance, and chelating agents. The use of a compatibility agent is particularly important if the nitrogen containing surfactant of the present invention is not very compatible in concentrated pesticide formulations. When using a compatibility agent, it is advantageous that the compatibility agent is a surfactant which can also enhance the efficacy of the pesticide. One such a preferred compatibility agent is C6-C12 dimethylamidopropylamine.

Unlike many other prior art surfactants, some of the surfactants of the present invention showed excellent compatibility without any help from a compatibility agent in concentrated aqueous glyphosate systems.

The use concentration of the surfactant of the present invention in a in-can pesticide formulations may be from about 0.005% to about 20%, preferably about 0.05 to about 15%, and more preferably about 0.5 to about 10% in % active basis. The use concentration of the surfactant of the present invention in a tank mix pesticide spray solution may be from about 0.001% to about 5%, preferably about 0.01 to about 2%, and more preferably about 0.1 to about 1% (in % active surfactant basis).

The surfactants of the invention may also be used with other surfactants such as alkylamine alkoxylate and their quaternary, anionic surfactant such as sulfate and sulfonate from alcohol and alkoxylated alcohol, phosphate ester and ethoxylated phosphate ester, nonionic surfactant such as alcohol alkoxylate and alkyl (C6-C18) polyglucoside, and silicone surfactant.

It is understood that a primary advantage of any of the surfactants mentioned above that are included in the invention is that the surfactant may be the only surfactant employed in the formulation.

It might also be the case that there is a synergy between the surfactants of the present invention and one or more other surfactants that renders the combination of surfactants more effective than either surfactant when used alone.

In the case that another surfactant is used together with the surfactants of the present invention, it is advantageous that the mixture of the surfactants have low aquatic toxicity and low irritation profiles. Employing the surfactants with low aquatic toxicity and low irritation profiles of the present invention in the formulation can reduce the total toxicity of a blend while keeping the efficacy more or less the same even if a not-so favorable surfactant in terms of the aquatic toxicity and irritation profiles is used in the blend.

The following non-limiting examples are presented to further illustrate and explain the present invention.

Example 1

Four glyphosate samples with various surfactants were sprayed on morning glory (IPOHE, a broad leaf week) and wheat (TRIAV, a narrow leaf grass) in a green house setting. The surfactants are designated in Table 1.

TABLE 1

Studied glyphosate formulations using various surfactants

| Sample | Description | Glyph:surf ratio |
|---|---|---|
| A | Glyphosate with Mono sodium lauryl iminodipropionate | 3:1 |
| B | Glyphosate with Coco diamine trimethyl betaines | 6.7:1 |
| C | Glyphosate with Tallowamine 15EO | 3:1 |
| D | Glyphosate (isopropylamine salt) alone without surfactant | |

The glyphosate rates of the spray solutions were 186, 372, and 743 g ae/ha (gram acid equivalent per hectare). The glyphosate to surfactant ratio was fixed at 3:1 except for sample B (coco diamine trimethyl betaines) which had a ratio of 6.7. Higher ratio means lower surfactant concentration. A ratio of 6.7 means the sample, at the same glyphosate concentration, has 2.2 times less surfactant than a sample with a ratio of 3.

Sample D served as a negative control, since it contained only glyphosate without added surfactant. Sample C served as a positive control since it is well known that tallowamine-15EO is an excellent surfactant to enhance glyphosate efficacy.

% Control ratings were conducted by an experienced person at 7, 14, 21, and 29 days after treatment (DAT). Digital pictures were also taken at the time of rating. Each % Control value was an average of 4 replicas.

The Mono sodium lauryl iminodipropionate of Sample A has the following nominal structure which can be obtained by reacting alkylamine with acrylic acid then neutralized with a base (NaOH).

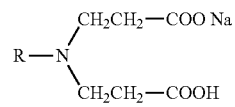

The Cocodiamine trimethyl betaines of Sample B has the following nominal structure which can be obtained by reacting N,N'N'-trimethyl cocodiamine with sodium monochloroacetate (SMCA):

(i)
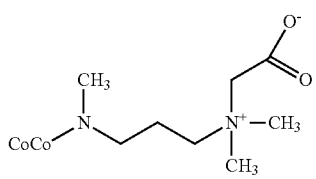

(ii)
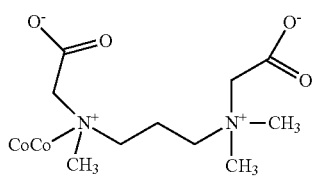

(iii)
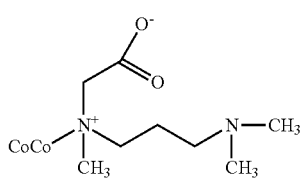

Where R=coco.

The Cocodiamine trimethyl betaines showed good adjuvancy for glyphosate even at very low use rate, and also speeded up glyphosate activity, as indicated in the following result.

Results are shown in Table 2.

TABLE 2

Bioefficacy result of example 1.

| Label | Glyphosate: surfactant | Species | Glyph rate, g ae/h | % Control 7DAT | % Control 14 DAT | % Control 21DAT | % Control 29DAT |
|---|---|---|---|---|---|---|---|
| A | 3 | MG | 186 | 60 | 73 | 81 | 55 |
| B | 6.7 | MG | 186 | 89 | 96 | 97 | 97 |
| C | 3 | MG | 186 | 91 | 97 | 98 | 99 |
| D |  | MG | 186 | 55 | 68 | 79 | 68 |
| A | 3 | MG | 372 | 63 | 74 | 86 | 78 |
| B | 6.7 | MG | 372 | 84 | 90 | 91 | 90 |
| C | 3 | MG | 372 | 79 | 86 | 93 | 89 |
| D |  | MG | 372 | 86 | 89 | 95 | 93 |
| A | 3 | MG | 743 | 83 | 93 | 96 | 97 |
| B | 6.7 | MG | 743 | 93 | 98 | 98 | 99 |
| C | 3 | MG | 743 | 98 | 99 | 99 | 99 |
| D |  | MG | 743 | 83 | 90 | 94 | 91 |
| A | 3 | WT | 186 | 48 | 86 | 91 | 93 |
| B | 6.7 | WT | 186 | 91 | 99 | 100 | 100 |
| C | 3 | WT | 186 | 89 | 96 | 98 | 99 |
| D |  | WT | 186 | 28 | 60 | 80 | 58 |
| A | 3 | WT | 372 | 63 | 84 | 92 | 95 |
| B | 6.7 | WT | 372 | 93 | 98 | 100 | 100 |
| C | 3 | WT | 372 | 93 | 100 | 100 | 100 |
| D |  | WT | 372 | 58 | 85 | 89 | 89 |
| A | 3 | WT | 743 | 92 | 100 | 100 | 100 |
| B | 6.7 | WT | 743 | 96 | 100 | 100 | 100 |
| C | 3 | WT | 743 | 97 | 100 | 100 | 100 |
| D |  | WT | 743 | 84 | 94 | 98 | 98 |

The results are shown at FIGS. 1-6.

It can be seen from FIGS. 1-6 that for a given plant, a given glyphosate to surfactant ratio and a given glyphosate rate there will be an embodiment of the invention having at least as high a % control as glyphosate alone.

Example 2

Three concentrated glyphosate samples were studied and are shown in Table 3.

TABLE 3

Studied glyphosate formulations using various surfactants

| Label | Description | Glyph:surf ratio |
|---|---|---|
| A | Roundup Original (with tallowamine-15EO) | 3:1 |
| B | Glyphosate alone without surfactant |  |
| C | Glyphosate with tallow diamine trimethyl di-betaine | 13:1 |

The concentrated glyphosate samples were diluted to two glyphosate rates and sprayed in a green house so that the final glyphosate rates of the spray solutions were 489 and 978 g ae/H. Three samples at two rates equals six treatments that were sprayed on each of two species, morning glory (IPOHE, a broad leaf week) and winter wheat (TRZAW, a narrow leaf grass). Two rates were employed, 978 g ae/H, and 16-30 at 489 g ae/ha.

The glyphosate to surfactant ratio was fixed at 3:1 except for sample C (tallow trimethyl di-betaine) which had a ratio of 13:1. Higher ratio means lower surfactant concentration. A ratio of 13:1 means the sample, at the same glyphosate concentration, has 4.3 times less surfactant than a sample with a ratio of 3:1.

Sample A (glyphosate with added tallowamine-15EO) served as a positive control. Sample B containing only glyphosate without added surfactant served as a negative control.

The tallow diamine trimethyl di-betaine of Sample C was a 30% active material in water (with some NaCl) and its nominal structure is shown in the following:

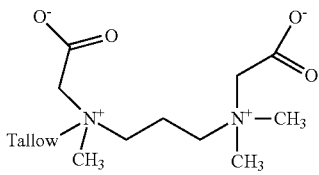

Figure 7:
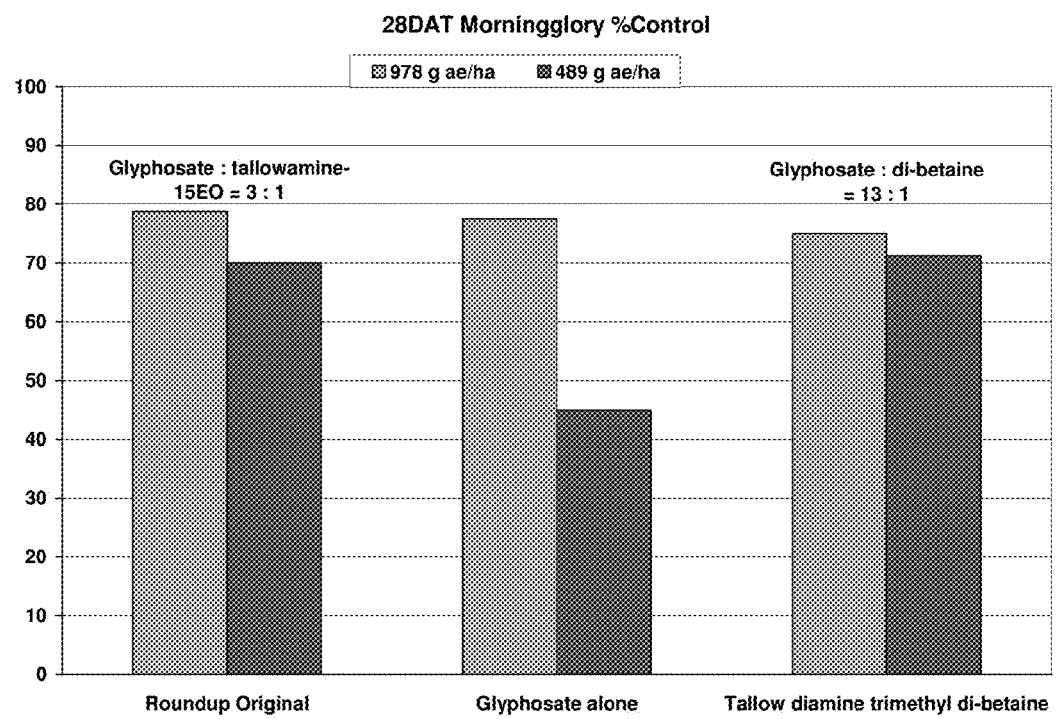
FIG. 7 is a bar graph illustrating the % control results of applying the glyphosate formulations of Table 3 at 489 g ae/ha and 978 g ae/ha to morning glory at 28 days after treatment.
Figure 8:
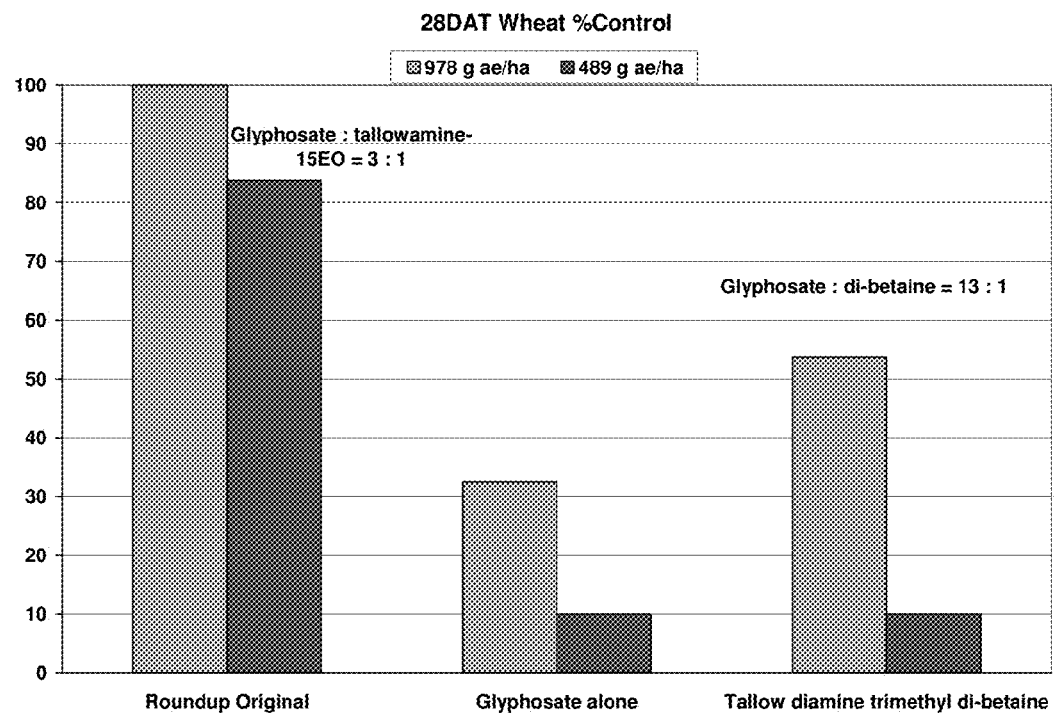
FIG. 8 is a bar graph illustrating the % control results of applying the glyphosate formulations of Table 3 at 489 g ae/ha and 978 g ae/ha to wheat at 28 days after treatment.

FIGS. 7-8 illustrates the % control results at 28 DAT. It can be seen that tallow diamine trimethyl di-betaine enhanced glyphosate bioefficacy even at very low rate.

Example 3

Glyphosate formulation containing oleylamphopolycarboxy glycinate (Na salt) was compared in a green house trial with glyphosate formulation containing tallowamine-10EO (as positive control) and glyphosate alone in terms of % Control. Three glyphosate rates were used, 930 g ae/ha, 465 gae/ha, and 233 g ae/ha.

The nominal structure in Oleylamphopolycarboxyglycinate (30% active, 10% NaCl, 60% H2O) is shown in the following:

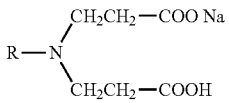

Figure 9:
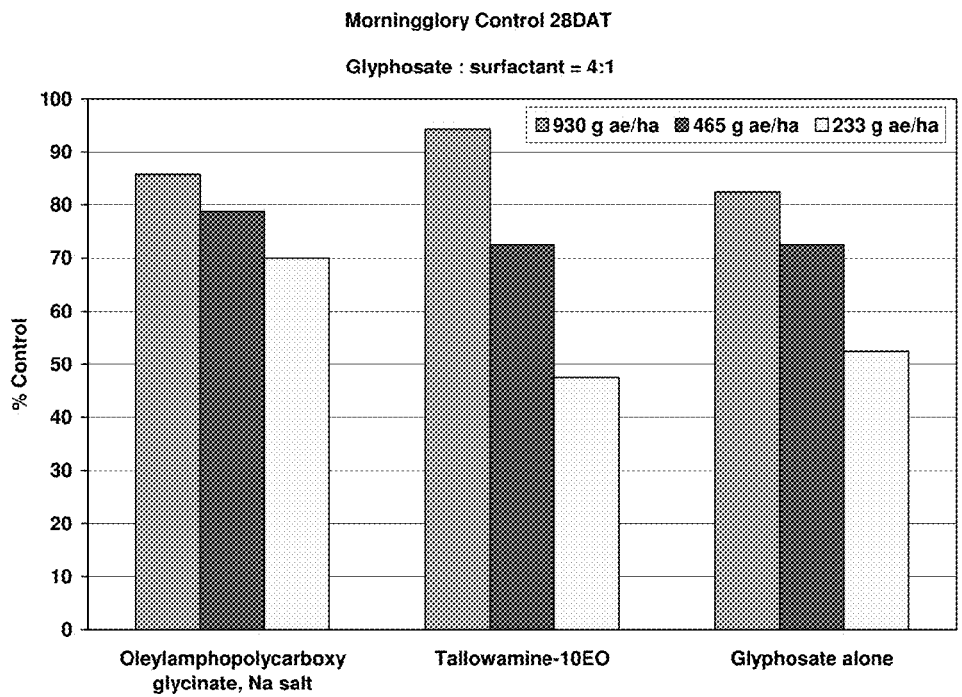
FIG. 9 is a bar graph illustrating the % control results of applying glyphosate formulation containing oleylamphopolycarboxy glycinate, glyphosate formulation containing tallowamine-10EO, and glyphosate alone, each at 233 g ae/ha, 465 g ae/ha, and 930 g ae/ha to morning glory at 28 days after treatment.
Figure 10:
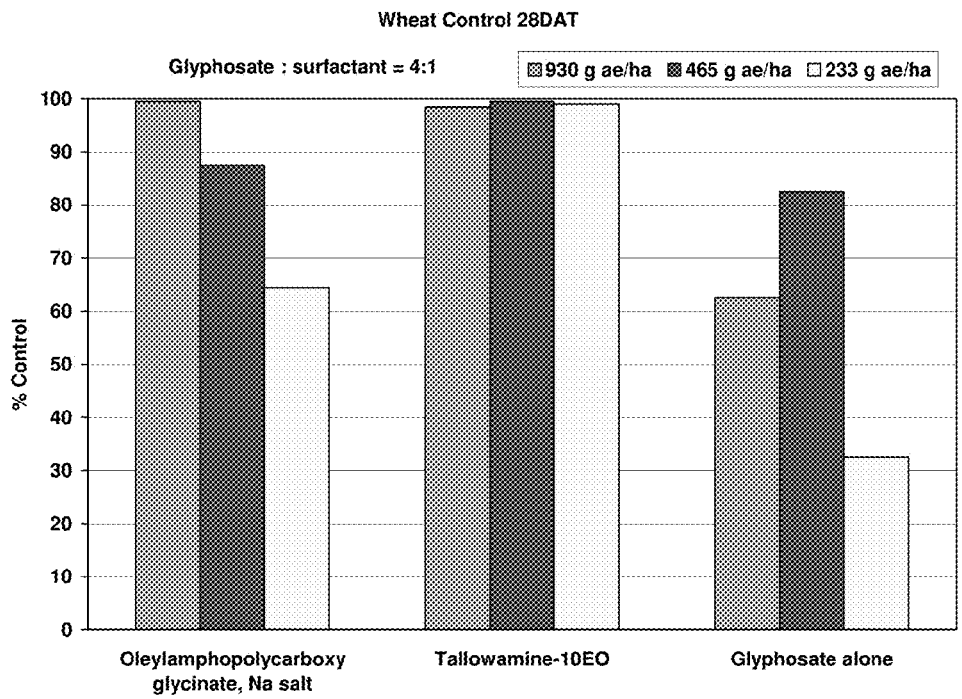
FIG. 10 is a bar graph illustrating the % control results of applying glyphosate formulation containing oleylamphopolycarboxy glycinate, glyphosate formulation containing tallowamine-10EO, and glyphosate alone, each at 233 g ae/ha, 465 g ae/ha, and 930 g ae/ha to wheat at 28 days after treatment.

The results are plotted in FIGS. 9-10.

This data showed that oleylamphopolycarboxy glycinate (Na salt) enhanced glyphosate efficacy when compared with the glyphosate formulation without surfactant.

Example 4

Five concentrated glyphosate samples were studied and they are shown in Table 4.

TABLE 4

Studied glyphosate formulations using various surfactants (glyphosate:surfactant ratio = 4:1)

| Label | Description |
|---|---|
| A | Armoteric CL8 |
| B | Mono sodium lauryl iminodipropinate |
| C | Tallowamine-15EO |
| D | Glyphosate alone without surfactant |
| E | Glyphosate with tallow diamine trimethyl di-betaine |

Figure 11:
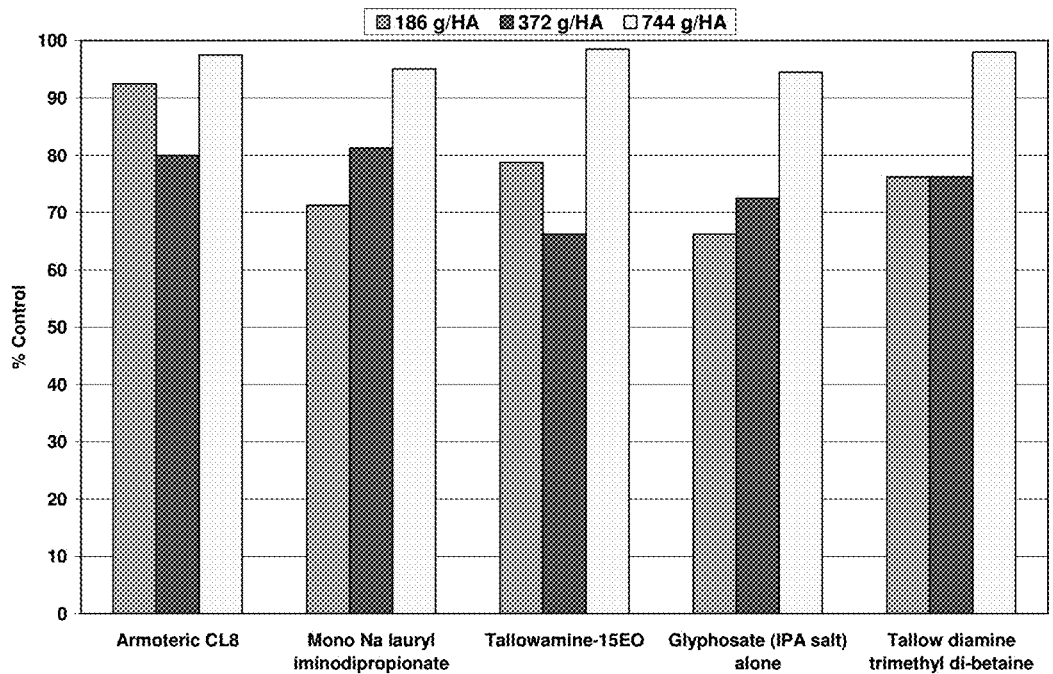
FIG. 11 is a bar graph illustrating the % control results of applying the glyphosate samples of Table 4 at 186 g/HA, 372 g/HA, and 744 g/HA to morning glory at 28 days after treatment.
Figure 12:
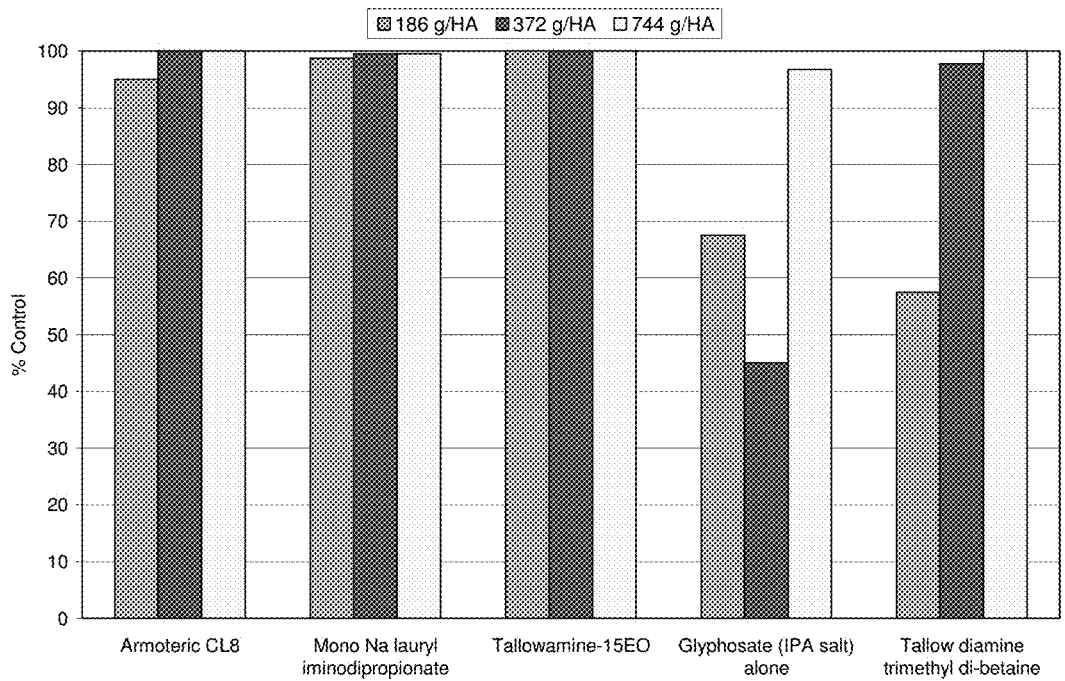
FIG. 12 is a bar graph illustrating the % control results of applying the glyphosate samples of Table 4 at 186 g/HA, 372 g/HA, and 744 g/HA to wheat at 28 days after treatment.

28DAT data at three glyphosate rates are plotted in FIGS. 11-12.

The nominal structure of Armoteric CL8 is shown in the following, and it can be obtained by reacting Coco-NH—C8 with acrylic acid then neutralized with NaOH.

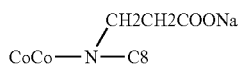

Nominal structures for Mono sodium lauryl iminodipropinate and tallow diamine trimethyl di-betaine can be found in Examples 1 and 2, respectively.

Example 5

Cocoamine-6EO betaine was compared in the same trial with tallowamine-15EO as the positive control and the surfactant-free sample as negative control in glyphosate formulations. Glyphosate to surfactant ratio was 3:1.

The nominal structure in Ethoxylated cocoamine (6EO) betaine is showed in the following:

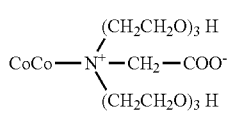

Figure 13:
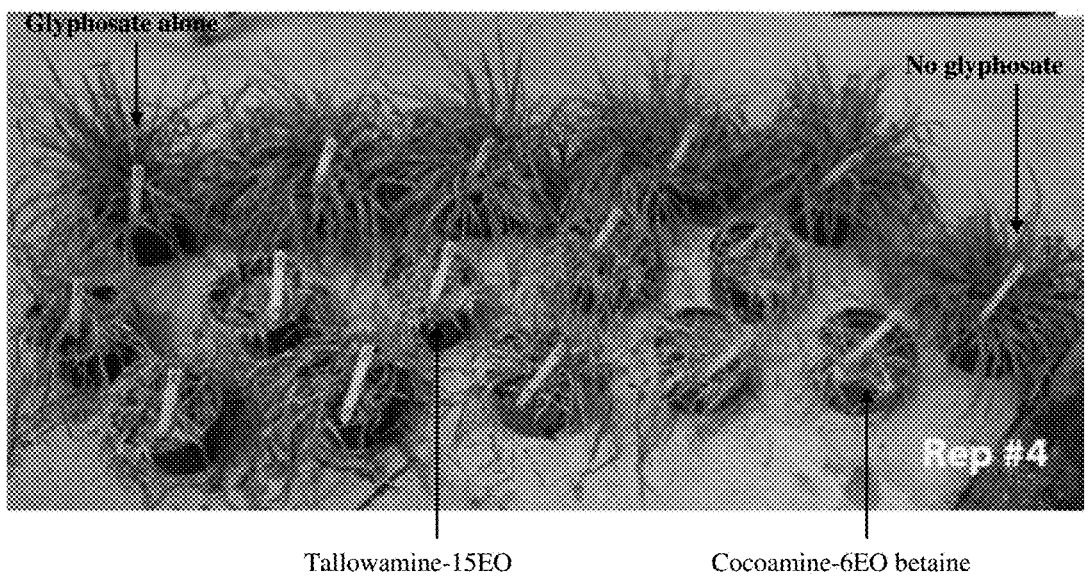
FIG. 13 is a photo of wheat taken at 21 days after treatment with glyphosate alone, glyphosate with tallowamine-15EO, glyphosate with cocoamine-6EO betaine, and no glyphosate.

The result showed that at a rate of 168 g ae/ha, glyphosate formulations containing cocoamine-6EO betaine and tallowamine-15EO both gave excellent control to wheat while glyphosate sample without surfactant did not give much control. This can be seen from the picture at FIG. 13, taken at 21DAT.

Example 6

This example shows the advantage of the surfactants of the present invention over those of the prior art in high load glyphosate (ammonium and potassium salts) formulations. The studied samples and results are showed in the following table.

TABLE 5

Compatibility study of some of the surfactants of the present invention and surfactants of prior art.

| | #1 | #2 | #3 | #4 | #5 | #6 | #7 | #8 |
|---|---|---|---|---|---|---|---|---|
| Di-NH4-glyphosate | 32.3 | | 32.2 | | 28.6 | 23.4 | | |
| K-glyphosate | | 40.4 | | 33.2 | | | 25.8 | 31.2 |
| Water | 61.4 | 55.1 | 61.4 | 57.8 | 62.4 | 74.3 | 72.8 | 68 |
| Cocoamphopolycarboxy glycinate | 6.3 | 4.5 | | | | | | |
| Cocoiminopropionate | | | 6.4 | 9 | | | | |
| Mono sodium C12 iminodipropionic (active compound in Deriphat 160C) | | | | | 9 | | | |

TABLE 5-continued

Compatibility study of some of the surfactants of the present invention and surfactants of prior art.

|  | #1 | #2 | #3 | #4 | #5 | #6 | #7 | #8 |
|---|---|---|---|---|---|---|---|---|
| Sodium Lauroamphoacetate (active compound in Minanol L-32) |  |  |  |  |  |  | 2.3 | 1.4 |
| Disodium Cocoamphodiacetate (active compound in Miranol C2M conc) |  |  |  |  |  |  |  | 0.8 |
| Appearance @ 25 C. | Clear | Clear | Clear | Clear | Clear | Hazy | Hazy | Hazy |

The chemical structures of Cocoamphopolycarboxyglycinate are shown in the following:

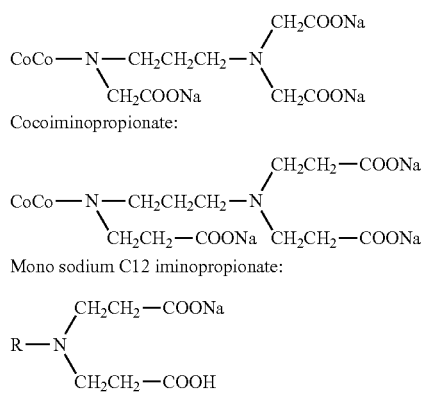

1 to #5 represent the present invention while #6-#8 represent the prior art. A hazy appearance indicates lack of compatibility.

Example 7

This example shows that an incompatible surfactant of the present invention can be made compatible with the addition of a small amount of a compatibility agent, C6-C9 dimethylamidopropylamine. The studied samples and results are shown in the following table.

TABLE 6

Effect of compatibility agent on the solubility of Mono sodium lauryl iminodipropinate in concentrated K-glyphosate formulation

|  | #1 | #2 | #3 | #4 |
|---|---|---|---|---|
| K-glyphosate | 29.6% | 29.6% | 29.6% | 29.6% |
| Water | 70.02% | 69.65% | 69.65% | 44.1% |
| Deriphat 160C | 0.38% | 0.38% | 0.38% | 24.3% |
| C6-9 dimethylamidopropylamine |  | 0.37% |  | 2% |
| Sodium hydroxide |  |  | 0.37% |  |
| Appearance at 25° C. | Hazy | Clear | Hazy | Clear |

In this example, Deriphat 160C® (30% Mono sodium lauryl iminodipropinate in water manufactured by Cognis Co.) could not be dissolved in 29.6% K-glyphosate (aq.) if the concentration of Deriphat 160 C was >0.38% (#1 in the table). With the addition of 0.37% C6-9 dimethylamidopropylamine, the hazy formulation became a clear solution (#2). #3 showed that pH effect is not the main reason for the dissolution of the insoluble species in K-glyphosate formulation. This concentration of surfactant in #1 was much too low to offer any benefit to glyphosate efficacy. In order for a surfactant to offer consistent benefit to glyphosate efficacy, the surfactant concentration typically has to be about greater than 7%. However, more than 24.3% Deriphat could be dissolved in the 29.6% K-glyphosate (aq.) if 2% C6-C9 dimethylamidopropylamine was added as the compatibility agent (#4).

The invention claimed is:

1. A method of enhancing the efficacy of agricultural formulations comprising at least one agricultural active, said method comprising adding to said formulation a nitrogen containing surfactant having the following general structure:

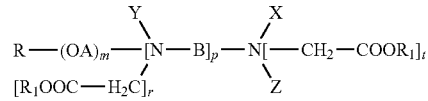

where R is C6-C22 linear or branched, saturated or non-saturated hydrocarbon group; A=C1-C3 linear or branched alkylene; m=0-10; B=C2-C6 alkylene; p=1-5; r=0-1; t=0-1; $R_1$ is nothing, hydrogen or $CH_3$ and the whole molecule has a chloride as the counter ion for each hydrogen when $R_1$ is hydrogen; and X=Y=Z=methyl.

2. The method of claim 1 wherein p=1 and B is C3 alkylene.

3. The method of claim 1 wherein said agricultural active comprises glyphosate, 2,4-D, dicamba, glufosinate, atrazine, or a mixture thereof.

4. The method of claim 1 wherein said agricultural formulation is a herbicide, fungicide, or insecticide formulation.

5. The method of claim 1 wherein said surfactant is the only surfactant when used in the agricultural formulations.

6. The method of claim 1 wherein said surfactant is used in agricultural formulations together with another surfactant comprising an alkyl dimethyl amidopropylamine wherein the alkyl group is selected from one or more of C5 to C12.

7. The method of claim 1 wherein the nitrogen containing surfactant is a cocodiamine trimethyl betaine.

8. The method of claim 1 wherein the nitrogen containing surfactant is a tallow diamine trimethyl di-betaine.

* * * * *